United States Patent [19]

Ecker et al.

[11] Patent Number: 5,691,461

[45] Date of Patent: Nov. 25, 1997

[54] OLIGONUCLEOTIDES INHIBITING CANDIDA GERM TUBE FORMATION

[75] Inventors: David J. Ecker, Leucadia, Calif.; Glenn D. Hoke, Mount Airy, Md.

[73] Assignee: ISIS Pharmaceuticals, Inc., Carlsbad, Calif.

[21] Appl. No.: 229,145

[22] Filed: Apr. 18, 1994

Related U.S. Application Data

[63] Continuation of Ser. No. 958,131, filed as PCT/US91/05802, Aug. 15, 1991, abandoned, which is a continuation-in-part of Ser. No. 568,672, Aug. 16, 1990, abandoned.

[51] Int. Cl.$^6$ .................................................. C07H 21/04
[52] U.S. Cl. ........................... 536/24.32; 536/23.74; 536/24.5
[58] Field of Search ................. 514/44; 536/23.1, 536/23.7, 23.74, 23.2, 23.4, 24.1, 24.2, 24.3, 24.32, 25.3, 25.4, 24.5; 435/6

[56] References Cited

U.S. PATENT DOCUMENTS

| | | | |
|---|---|---|---|
| 5,403,710 | 4/1995 | Weisburg et al. | 435/6 |
| 5,405,745 | 4/1995 | Gorman et al. | 435/6 |

OTHER PUBLICATIONS

Sugita, Y. et al., *J. Med. Vet. Mycology*, 31: 353–58, 1993.
Stein, C.A. et al., *Science*, 261: 1004–1012, 1993.
Buchman, T.G. et al., *Surgery*, 108 (2): 338–346, Aug. 1993.
Tseng, B.Y. et al., *Cancer Gene Therapy*, 1 (1): 65–71, 1994.
Mason, M. et al., *J. Clin. Micro.*, 25 (3): 563–566, 1987.
Burgener–Kairvz, P. et al., *J. Clin. Micro.*, 32: 1902–1907, 1994.
Kan, V.L., *J. Infectious Disease*, 168: 779–83, 1993.
Jordan, J.A. et al., *J. Clin. Micro.*, 32 (12): 2962–2967.
Chen, C. et al., *DNA*, 7(9): 617–26, 1988.
Uhlmann et al. (Jun., 1990), *Chemical Reviews*, vol. 90 (#4):543–584.

Au–Young et al., "Isolation of a Chitin Synthase Gene (CHS1) from Candida Albicans by Expression in Saccharomyces Cherevisiae", *Molecular Microbiology*, (1990) 4(2):197–207.

Gu et al., "Gene and Derived Peptide Sequences for C. Tropicalis Vacoular ATPase Subunit B", *Nucleic Acids Research*, (1990) 18(24):7446.

Jessus et al, "Specific Inhibition of Beta–Tubulin Synthesis in Xenopus Oocytes Using Anti–sense Oligodeoxyribonucleotides," *Gene* (1988) 72:311–312.

Lai et al., "Nucleotide Sequence of Cytochrome P450 LIA1 (lanosterol 14α–demethylase) from Candida Albicans," *Nucleic Acids Research* (1989) 17(2):804.

Losberger et al., "Sequence of the Candida Albicans Gene Encoding Actin", *Nucleic Acids Research*, (1989) 17:9488.

(List continued on next page.)

*Primary Examiner*—Stephen G. Walsh
*Attorney, Agent, or Firm*—Woodcock Washburn Kurtz Mackiewicz & Norris

[57] ABSTRACT

Compositions and methods are provided for the treatment and diagnosis of Candida infections. In accordance with preferred embodiments, oligonucleotides are provided which are specifically hybridizable with at least a portion of a Candida mRNA. Preferred targets are the mRNAs which encode β-tubulin, aspartate protease, actin and chitin synthetase, as well as the mRNA's which encode the ribosomal L25 protein, translation elongation factors 1 and 2 (TEF1 and TEF2), the b subunit of ATPase, and cytochrome P450 lanosterol 14α-demethylase (L1A1). The oligonucleotides comprise nucleotide units sufficient in identity and number to effect said specific hybridization. In other preferred embodiments, the oligonucleotides are specifically hybridizable with a transcription initiation site, a translation initiation site, 5'-untranslated sequences, 3' untranslated sequences, 5' cap, and intron/exon junction of the mRNAs. Methods of treating animals suffering from Candida infection are disclosed.

7 Claims, 4 Drawing Sheets

OTHER PUBLICATIONS

Lott et al., "Nucleotide Sequence of the Candida Albicans Aspartyl Proteinase Gene", *Nucleic Acids Research*, (1989) 17(4):1779.

Marcus–Sekura et al., "Comparative Inhibition of Chloramphenicol Acetyltransferase Gene Expression by Andisense Oligonucleotide Analogues Having Alkyl Phosphotriester, Methulphosphonate and Phosphorothioate Linkages", *Gene* (1988) 72:311–312.

Meunier, F., "Candidiasis", *Eur. J. Clin. Microbiol. Infect. Dis.* (1989) 8:438–447.

Nielsen, P.E., "Sequence–Selective Recognition of DNA by Strand Displacement with a Thymine–Substituted Polyamide", *Science* (1991) 254:1497–1500.

Radentz, W., "Opportunistic Fungal Infections in Immunocompromised Hosts", *Am. Acad. of Dermatology* (1989) 20(6):989–1003.

Rothenberg et al., "Oligodeoxynucleotides as Anti–Sense Inhibitors of Gene Expression: Therapeutic Implications", *J. Natl. Cancer Inst.* (1989) 81(20):1539–1544.

Smith et al., "Isolation and Characterization of a β–Tubulin Gene from candida Albicans", *Gene* (1988) 63:53–63.

Sundstrom et al., "Sequence Analysis and Expression of the Two Genes for Elongation Factor 1α from the Dimorphic Yeast Candida Albicans", *J. Bacteriol.* (1990) 172:2036–2045.

Van't Wout et al., "Effect of Amphotericin B, Fluconazole and Itrconazole on Intracellular Candida Albicans and Germ Tube Development in Macrophages", *J. Antimicrob. Chemotherapy* (1990) 25:803–811.

Wong et al, "Sequence of the gene for the cytoplasmic Ribosomal RNA Small Subunit from Candida (Torulopsis) Glabrata", *Nucleic Acids Research* (1990) 18(7):1888.

Woudt et al., "Structural and Putative Regulatory Sequences of the Gene Encoding Ribosomal Protein L25 in Candida Utilis", *Curr. Genet.* (1987) 12:193–198.

Zon, G., "Oligonucleotide Analogues as Potential Chemotherapeutic Agents", *Pharmaceutical Research* (1988) 5(9):539–549.

FIG. 1A

```
   1  TTATATCAAA TAGATTTAGA TTTTTTTATT TTAAAGAATT TTTTAATCAA
  51  GAAATCAATA TCAACATTAT AGAACTATGA GAGAAATTGT ATGTTCCGTT
 101  TATTCCCTTC CTTACACCAA ATCATTGGAA TCCTTATGTG TTTTGTTGTT
 151  GTTGTCTGAA AATTTTTGGT TCTGTTTTAC GCGCCTTTTT CGACTAAATT
 201  GATTCAAATA GGATTCCCTA ATGATTAAT GATTTGTGTC AATCAATCAA
 251  TGTTTTATTA AGTTTTATCA AATATACTAA CTGCTTTTGC CCTTTTTTTT
 301  AGATTCATTT ATCAACTGGT CAATGTGGTA ATCAAATTGT ATGTATAAAC
 351  ACTGAAGAAA AAAAAATTCT ATCATTGTTA TGTTGTGATC TTTGATCTTT
 401  AGTTGTCGGG TTAACACCTG CCAATTGGAT CAATACATCA ATCAATTAAT
 451  TCTAATCTTG AAAAAAAAAT TGATTTTACT AACAATTTTT TCTTTTATTT
 501  AGGGTGCTGC CTTTTGGGAA ACTATTTGTG GAGAACATGG ATTAGATAAC
 551  AATGGAACTT ATGTTGGAAA TAATGAACTT CAAAAATCCA AATTAGACGT
 601  TTATTTCAAC GAAGCTACTT CTGGGAAATA CGTTCCTCGT GCCGTTTTAG
 651  TCGATTTGGA ACCAGGTACT ATTGATAATG TGAAAACTTC ACAAATTGGT
 701  AACTTGTTTA GACCAGATAA CTTTATTTTC GGTCAAAGTT CTGCCGGCAA
 751  TGTTTGGGCT AAAGGTCATT ACACTGAAGG TGCTGAATTA GTTGATTCTG
 801  TTTTAGATGT TGTTAGAAGA GAAGCTGAAG GCTGTGATTC TTTACAAGGT
 851  TTCCAAATCA CCCATTCTTT GGGTGGTGGT ACTGGTTCTG GTATGGGTAC
 901  TTTGTTGATT TCTAAAATTA GAGAAGAATT CCCTGATACA ATGATGGCCA
 951  CTTTTTCTGT TGTCCCATCA CCAAAAGTTT CCGATACCGT TATTGAACCA
1001  TATAACGCTA CTTTATCAGT CCATCAATTG GTTGAAAACT CTGATGAAAC
1051  TTTCTGTATT GATAATGAAG CCTTGTACAA TATTTGTCAA AACACTTTGA
1101  AATTACCACA ACCATCTTAT GCTGAATTGA ACAATTTGGT TTCTTCTGTC
1151  ATGTCTGGTG TTACTACTTC TTTACGTTAT CCAGGTCAAT TGAATTCGGA
1201  TTTAAGAAAA TTGGCAGTCA ATTTGGTTCC ATTCCCAAGA TTACATTTCT
```

FIG. 1B

```
1251  TTATGGTTGG TTATGCTCCA TTGACTTCTA TGGGTTCTAA ATCTTTCAGA
1301  TCAGTCACCG TCCCAGAATT GACTCAACAA ATGTTTGATG CCAAAAATAT
1351  GATGGCTGCT TCTGATCCAA GAAATGGTCG TTATTTAACT GTTGCTGCCT
1401  TTTTCAGAGG TAAAGTATCT GTTAAAGAAG TTGACGATGA AATGCACAAA
1451  ATCCAAACCA GAAACTCATC TTATTTTGTT GATTGGATTC CAAATAATGT
1501  TCAAACTGCT GTTTGTTCAG TTCCTCCAAA AGATTTGGAT ATGTCTGCTA
1551  CTTTTATTGG AAACTCTACT TCCATTCAAG AATTATTTAA AAGAGTTGGT
1601  GATCAATTCA GTGCTATGTT CAGAAGAAAA GCTTTCTTGC ATTGGTATAC
1651  TTCTGAAGGT ATGGATGAAA TGGAATTTAC TGAAGCTGAA TCTAATATGA
1701  ATGATTTGGT TAGTGAATAC CAACAATACC AAGAAGCTAG TATTGATGAA
1751  GAAGAATTAG AATATGCCGA TGAAATCCCA TTAGAAGATG CCGCCATGGA
1801  ATAAAAGCTG ATAAATGCTA CAATATTAAT TAATTATAAT TTTTTTTTTT
1851  GTTCACTTCT AATATAATTA TGGTTTTTTT TGGTTTAG
```

OLIGONUCLEOTIDES INHIBITING CANDIDA GERM TUBE FORMATION

This is a continuation of application Ser. No. 07/958,131, now abandoned, filed Oct. 9, 1992 which is a Continuation-in-Part of Ser. No. 07/568,672, filed Aug. 16, 1990, now abandoned, and a Continuation-in-Part of Ser. No. PCT/US91/05802 filed Aug. 15, 1991, each of which applications is assigned to the assignee of the present invention.

FIELD OF THE INVENTION

This invention relates to diagnostics, research reagents, and therapies for Candida infections. In particular, this invention relates to antisense oligonucleotide interactions with certain Candida messenger ribonucleic acids. Specifically, antisense oligonucleotides are designed to hybridize to the Candida mRNA's which encode the β-tubulin, actin, chitin synthetase and aspartate protease proteins. Other antisense oligonucleotides are designed to hybridize specifically to the Candida mRNA's which encode the ribosomal L25 protein, translation elongation factors 1 and 2 (TEF1 and TEF2), the b subunit of ATPase, and cytochrome P450 lanosterol 14α-demethylase (L1A1). These oligonucleotides have been found to lead to the modulation of the activity of the Candida RNA or DNA, and thus to the modulation of the Candida infection. Palliation and therapeutic effect result.

BACKGROUND OF THE INVENTION

Opportunistic infections in immunocompromised hosts represent an increasingly important cause of mortality and morbidity. Candida species are among the most common of the fungal pathogens with *Candida albicans* as the most common species, but with *Candida tropicalis*, *Candida krusei*, *Candida glabrata* (*Torulopsis glabrata*) and *Candida parapsilosis* also found in infected individuals. Candida is responsible for a variety of nosocomial infections. For a general review of the types & severity of Candida infections see Meunier, F., *Eur. J. Clin. Microbiol. Infect. Dis.* 8:438–447 (A89) or Radentz, W., *J. Am. Acad. Derm.* 20:989–1003. Cancer patients, particularly leukemia patients, are at high risk of Candida infections. Up to 30% of all leukemia patients show evidence of invasive candidiasis upon autopsy. Cancer patients with a variety of solid tumors also are at risk of opportunistic infection. Improvements in the treatment of cancer, with greater use of surgery and newer chemotherapies, has resulted in increasing numbers of non-terminal patients becoming infected with Candida and requiring treatment.

Another group at risk for Candida and other opportunistic infections is the AIDS population. In AIDS patients Candida is a problem in oropharyngeal infections. Burn patients, I.V. drug users, persons with catheters and premature neonates are all also susceptible to infection by Candida.

Candida can also be problematic in the non-immunocompromised host. In normal healthy women, Candida is responsible for vulvovaginitis. The overwhelming majority of yeasts which infect the vagina are isolates of *Candida albicans*. This problem is often exacerbated by pregnancy, the use of oral contraceptives or in disease situations requiring the use of antibiotics, all of which increase the probability of an infection by Candida.

There are currently several drugs in use for managing Candida infections. Amphotericin B is generally considered the standard therapy for systemic Candida infection. However, amphotericin B has a number of severe side effects, some of which cause permanent damage to the patients' liver and kidneys. Moreover, the efficacy of amphotericin B is limited and treatment does not always result in elimination of the infection. Therefore, there is a great need for agents which are effective in inhibiting Candida infections but do not cause toxic side effects to the host. Antisense oligonucleotides hold great promise as therapeutic agents for Candida infections. There have been no prior attempts to inhibit Candida with antisense oligonucleotides. Accordingly, there has been and continues to be a long-felt need for the design of oligonucleotides which are capable of effective therapeutic use.

OBJECTS OF THE INVENTION

It is an object of this invention to provide oligonucleotides which are capable of hybridizing with messenger RNA of Candida to inhibit the function of the messenger RNA.

It is a further object to provide oligonucleotides which can modulate the expression of Candida through antisense interaction with messenger RNA of the fungus.

Yet another object of this invention is to provide methods of diagnostics and therapeutics for Candida in animals. Methods, materials and kits for detecting the presence or absence of Candida in a sample suspected of containing it are further objects of the invention.

Novel oligonucleotides are other objects of the invention.

These and other objects will become apparent to persons of ordinary skill in the art from a review of the instant specification and appended claims.

SUMMARY OF THE INVENTION

In accordance with the present invention, oligonucleotides are provided which specifically hybridize with at least a portion of an RNA from Candida. The oligonucleotide is preferably designed to bind directly to Candida RNA.

This relationship is commonly denoted as "antisense." The oligonucleotides are able to inhibit the function of RNA—either its translation into protein, its translocation into the cytoplasm, or any other activity necessary to its overall biological function. The failure of the RNA to perform all or part of its function results in failure of a portion of the genome controlling the normal life cycle of the fungus.

It has been found to be preferred to target specific Candida RNA portions for antisense oligonucleotide attack. It has been discovered that the genes coding for β-tubulin, aspartate protease, actin and chitin synthetase are particularly useful for this approach. The genes encoding the ribosomal L25 protein, translation elongation factors 1 and 2 (TEF1 and TEF2), the b subunit of ATPase, and cytochrome P450 lanosterol 14α-demethylase (L1A1) are also particularly useful. Inhibiting translation of the mRNA's relating to these proteins is expected to be useful for the treatment of Candida infections.

Methods of modulating Candida infection comprising contacting the animal with an oligonucleotide hybridizable with nucleic acid of the fungus are provided. Oligonucleotides hybridizable with mRNA coding for β-tubulin, aspartate protease, actin and chitin synthetase proteins are preferred. Oligonucleotides hybridizable with mRNA coding for the ribosomal L25 protein, TEF1 and TEF2, the ATPase b subunit and cytochrome P450 L1A1 are also preferred.

BRIEF DESCRIPTION OF THE DRAWINGS

FIGS. 2 A and B are graphical representations of the effects of antisense oligonucleotides on Candida germ tube formation at oligonucleotide doses of 0.5 µM (A) and 1.0 µM (B).

DETAILED DESCRIPTION OF THE INVENTION

Antisense oligonucleotides hold great promise as therapeutic agents for the treatment of many human diseases. Oligonucleotides specifically bind to the complementary sequence of either pre-mRNA or mature mRNA, as defined by Watson-Crick base pairing, inhibiting the flow of genetic information from DNA to protein. Numerous recent studies have documented the utility of antisense oligonucleotides as biochemical tools for studying target proteins. Rothenberg et al., *J. Natl. Cancer Inst.* 1989, 81, 1539–1544; Zon, G., *Pharmaceutical Res.* 1988, 5, 539–549. Because of recent advances in oligonucleotide chemistry, synthesis of nuclease resistant oligonucleotides, and availability of types of oligonucleotide analogs which exhibit enhanced cell uptake, it is now possible to consider the use of antisense oligonucleotides as a novel form of therapeutics.

For therapeutics, an animal suspected of having a Candida infection is treated by administering oligonucleotides in accordance with this invention. Persons of ordinary skill can easily determine optimum dosages, dosing methodologies and repetition rates. Such treatment is generally continued until either a cure is effected or a diminution in the disease state is achieved.

It is to be expected that differences in the DNA of Candida from different species and from different types within a species exist. Thus, it is believed, for example, that the regions of the various Candida species serve essentially the same function for the respective species and that interference with expression of the genetic information will afford similar results in the various species. This is believed to be so even though differences in the nucleotide sequences among the species doubtless exist.

Accordingly, nucleotide sequences set forth in the present specification will be understood to be representational for the particular species being described. Homologous or analogous sequences for different species of Candida are specifically contemplated as being within the scope of this invention.

The present invention employs oligonucleotides for use in antisense inhibition of the function of Candida RNA. In the context of this invention, the term "oligonucleotide" refers to an oligomer or polymer of ribonucleic acid or deoxyribonucleic acid. This term includes oligomers consisting of naturally occurring bases, sugars and intersugar (backbone) linkages as well as oligomers having non-naturally occurring portions which function similarly. Such modified or substituted oligonucleotides are often preferred over native forms because of properties such as, for example, enhanced cellular uptake and increased stability in the presence of nucleases.

Specific examples of some preferred oligonucleotides envisioned for this invention may contain phosphorothioates, phosphotriesters, methyl phosphonates, chain alkyl or cycloalkyl intersugar linkages or short chain heteroatomic or heterocyclic intersugar linkages. Most preferred are those with $CH_2$—NH—O—$CH_2$, $CH_2$—N($CH_3$)—O—$CH_2$, $CH_2$—O—N($CH_3$)—$CH_2$, $CH_2$—N($CH_3$)—N($CH_3$)—$CH_2$ and O—N($CH_3$)—$CH_2$—$CH_2$ backbones (where phosphodiester is O—P—O—$CH_2$). Also preferred are oligonucleotides having morpholino backbone structures. Summerton, J. E. and Weller, D. D., U.S. Pat. No. 5,034,506. In other preferred embodiments, such as the protein-nucleic acid (PNA) backbone, the phosphodiester backbone of the oligonucleotide may be replaced with a polyamide backbone, the bases being bound directly or indirectly to the aza nitrogen atoms of the polyamide backbone. P. E. Nielsen, M. Egholm, R. H. Berg, O. Buchardt, Science 1991, 254, 1497. Other preferred oligonucleotides may contain alkyl and halogen-substituted sugar moieties comprising one of the following at the 2' position: OH, SH, $SCH_3$, F, OCN, $O(CH_2)_nNH_2$ or $O(CH_2)_nCH_3$ where n is from 1 to about 10; $C_1$ to $C_{10}$ lower alkyl, substituted lower alkyl, alkaryl or aralkyl; Cl; Br; CN; $CF_3$; $OCF_3$; O-, S-, or N-alkyl; O-, S-, or N-alkenyl; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. Oligonucleotides may also have sugar mimetics such as cyclobutyls in place of the pentofuranosyl group.

The oligonucleotides in accordance with this invention preferably comprise from about 5 to about 50 nucleic acid base units. It is more preferred that such oligonucleotides comprise from about 8 to 25 nucleic acid base units, and still more preferred to have from about 12 to 25 nucleic acid base units. As will be appreciated, a nucleic acid base unit is a base-sugar combination suitably bound to adjacent nucleic acid base unit through phosphodiester or other bonds.

The oligonucleotides used in accordance with this invention may be conveniently and routinely made through the well-known technique of solid phase synthesis. Equipment for such synthesis is sold by several vendors including Applied Biosystems. Any other means for such synthesis may also be employed, however the actual synthesis of the oligonucleotides are well within the talents of the routineer. It is also well known to use similar techniques to prepare other oligonucleotides such as the phosphorothioates and alkylated derivatives.

In accordance with this invention, persons of ordinary skill in the art will understand that messenger RNA identified by the open reading frames (ORFs) of the DNA from which they are transcribed includes not only the information from the ORFs of the DNA, but also associated ribonucleotides which form regions known to such persons as the 5'-untranslated region, the 3'- untranslated region, and intervening sequence ribonucleotides. Thus, oligonucleotides may be formulated in accordance with this invention which are targeted wholly or in part to these associated ribonucleotides as well as to the informational ribonucleotides.

In accordance with this invention, the oligonucleotide is specifically hybridizable with at least a portion of a nucleic acid of Candida. In preferred embodiments, the nucleic acid portion includes the mRNA's which encode β-tubulin, actin, chitin synthetase and aspartate protease proteins. In other preferred embodiments, the nucleic acid portion includes the mRNA's which encode the ribosomal L25 protein, TEF1 and TEF2, the b subunit of ATPase, and cytochrome P450 L1A1. Oligonucleotides comprising the corresponding sequence, or part thereof, are useful in the invention. Thus, the oligonucleotides of this invention are designed to be hybridizable with messenger RNA of Candida. Such hybridization, when accomplished, interferes with the normal function of the messenger RNA to cause a loss of its utility to the fungus. The functions of messenger RNA to be interfered with include all vital functions such as translocation of the RNA to the situs for protein translation, actual translation of protein from the RNA, splicing or other processing of the RNA, and possibly even independent catalytic activity which may be engaged in by the RNA. The overall effect of such interference with the RNA function is to cause the Candida to lose the benefit of the RNA and, overall, to experience interference with expression of its genome. Such interference is generally fatal to the fungus.

Figure 1A:
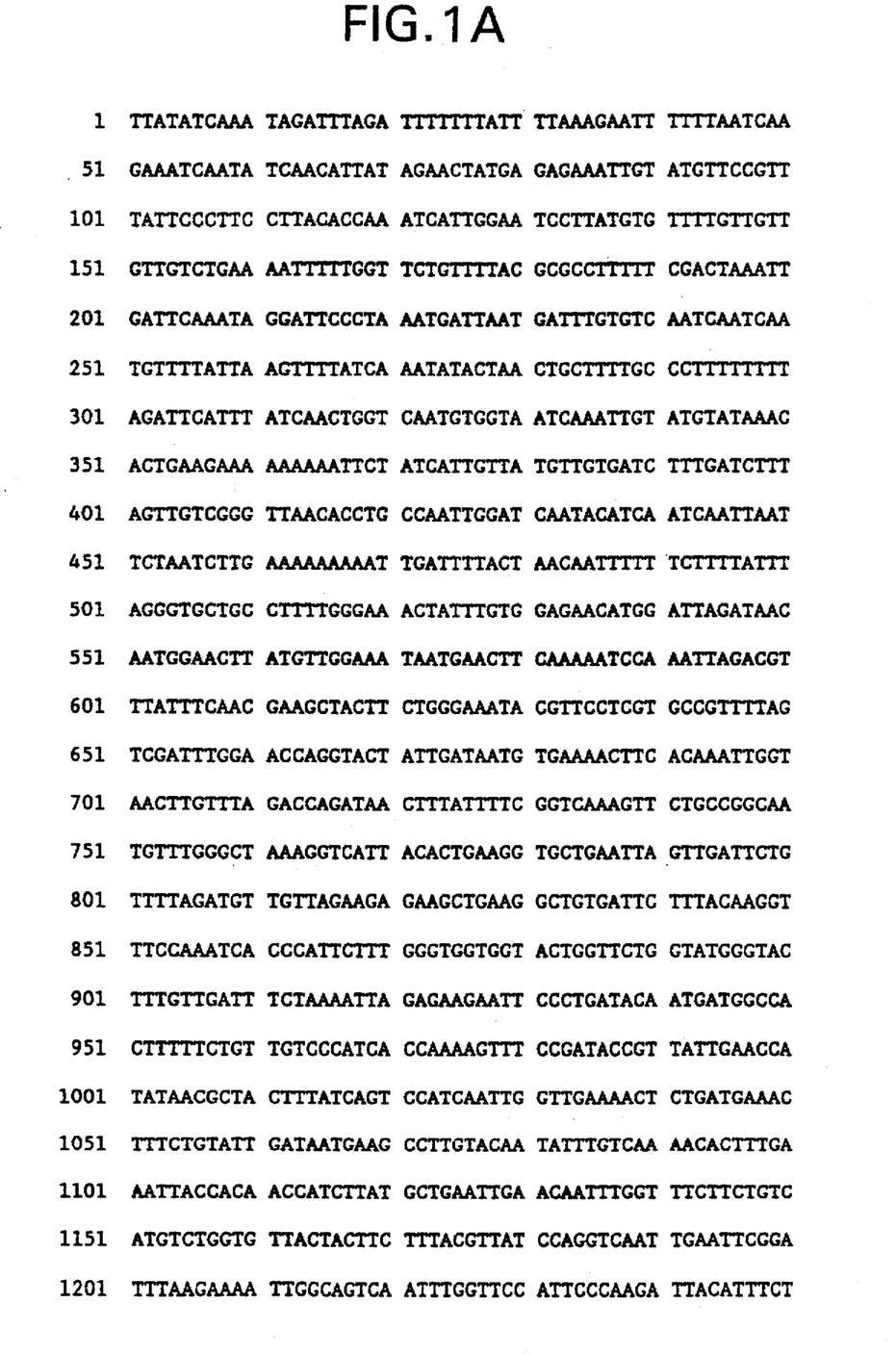
FIG. 1A and FIG. 1B show the sequence of the β-tubulin gene of *Candida albicans* SEQ ID NO:13.
Figure 1B:
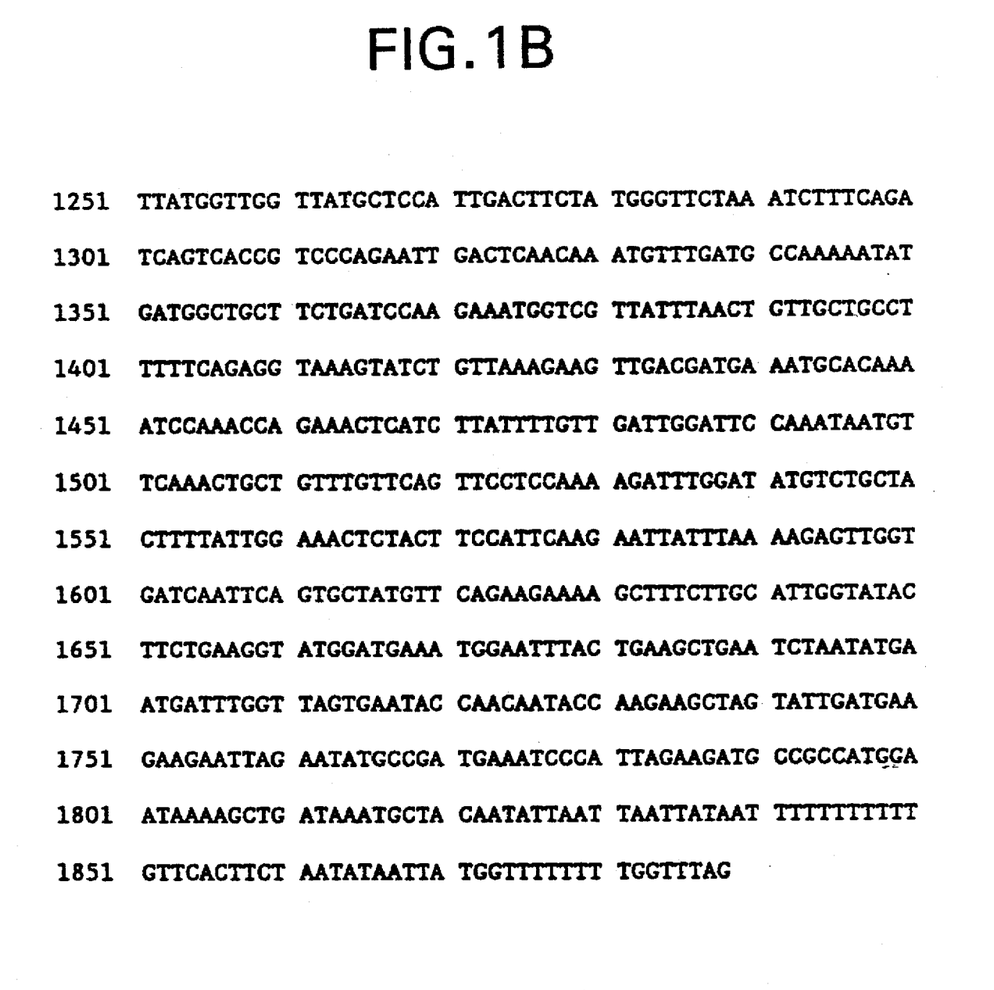

FIG. 1A and FIG. 1B show the sequence of the β-tubulin gene of Candida albicans SEQ ID NO:13. The sequence for the *Candida albicans* β-tubulin gene is known. Smith et al., *Gene* 1988, 63, 53–63. The gene sequence of *Candida albicans* is known. Au-Young et al., *Molecular Microbiology* 1990, 4, 197–207. The sequence for the *Candida albicans* actin gene is known as well. Losberger et al., *Nucl. Acid. Res.* 1989, 17, 9488. The sequence for the *Candida albicans* aspartyl proteinase gene is set forth in Lott et al., *Nucl. Acid Res.* 1989, 17, 1779. The sequence for the *Candida albicans* cytochrome P450 L1A1 is disclosed in Lai et al., *Nucl. Acid. Res.* 1989, 17, 804. The sequences for the *Candida albicans* elongation factors TEF1 and TEF2 are disclosed in Sundstrom et al., *J. Bacteriol.* 1990, 172, 2036. The sequence of the ribosomal L25 gene is known in *Candida glabrata* (*Torulopsis glabrata*) and *Candida utilis.* Wong et al., *Nucl. Acids Res.* 1990, 18, 1888; Woudt et al., *Curr. Genet.* 1987, 12, 193. The gene sequence for the *Candida tropicalis* vacuolar ATPase subunit b is disclosed in Gu et al., *Nucl. Acids Res.* 1990, 18, 7446.

Oligonucleotides useful in the invention are complementary to and comprise one of these sequences, or part thereof. Thus, it is preferred to employ any of these oligonucleotides as set forth above or any of the similar nucleotides which persons of ordinary skill in the art can prepare from knowledge of the preferred antisense targets for the modulation of the fungal infection.

The oligonucleotides of this invention can be used in diagnostics, therapeutics and as research reagents and kits. For therapeutic use, the oligonucleotide is administered to an animal suffering from a Candida infection. It is generally preferred to apply the therapeutic agent in accordance with this invention topically or intralesionally. Other forms of administration, such as transdermally, or intramuscularly may also be useful. Inclusion in suppositories is presently believed to be likely to be highly useful. Use of the oligonucleotides of this invention in prophylaxis is also likely to be useful. Such may be accomplished, for example, by providing the medicament as a coating in condoms and the like. Use of pharmacologically acceptable carriers is also preferred for some embodiments.

The present invention is also useful in diagnostics and in research. Since the oligonucleotides of this invention hybridize to nucleic acid from Candida, sandwich and other assays can easily be constructed to exploit this fact. Provision of means for detecting hybridization of oligonucleotide with Candida present in a sample suspected of containing it can routinely be accomplished. Such provision may include enzyme conjugation, radiolabelling or any other suitable detection systems. Kits for detecting the presence or absence of Candida may also be prepared.

Several preferred embodiments of this invention are exemplified in accordance with the following examples. The target mRNA species for modulation relates to the β-tubulin, actin, chitin synthetase and aspartate protease proteins of Candida. Other preferred mRNA targets relate to the ribosomal L25 protein, translation elongation factors 1 and 2 (TEF1 and TEF2), the b subunit of ATPase, and cytochrome P450 lanosterol 14α-demethylase (L1A1). Persons of ordinary skill in the art will appreciate that the present invention is not so limited, however, and that it is generally applicable. The inhibition of these Candida RNAs are expected to have significant therapeutic benefits in the treatment of disease. In order to assess the effectiveness of the compositions, an assay or series of assays is required.

The following are intended as nonlimiting examples of some embodiments of the invention.

EXAMPLES

Example 1

Inhibition of *Candida albicans* With Antisense Oligonucleotides Complementary to the mRNAs Coding For β-Tubulin, Actin, Chitin Synthetase and Aspartate Protease:

A series of antisense oligonucleotide sequences were selected which are complementary to the Candida β-tubulin, aspartate protease, actin and chitin synthetase mRNA's. These are shown in Table 1:

TABLE 1

Antisense Oligonucleotides Targeted to *Candida Albicans*

| COMPOUND | SEQUENCE (5'–3') | | | | | | | TARGET RNA | |
| --- | --- | --- | --- | --- | --- | --- | --- | --- | --- |
| 1275 SEQ ID NO:2 | CAA | TTT | CTC | TCA | TAG | TTG | TA | Tubulin | initiation of translation |
| 1276 SEQ ID NO:14 | CGG | AAC | ATA | CAA | TTT | CTC | TC | Tubulin | 5' splice junction intron 1 |
| 1277 SEQ ID NO:15 | CAA | AAG | CAG | TTA | GTA | TAT | TT | Tubulin | splice branch point intron 1 |
| 1278 SEQ ID NO:16 | AAA | AAT | TGT | TAG | TAA | AAT | CA | Tubulin | splice branch point intron 2 |
| 1279 SEQ ID NO:17 | CTA | AAA | AAA | AGG | GCA | AAA | GC | Tubulin | 3' splice junction intron 1 |
| 1280 SEQ ID NO:18 | TTC | CCA | AAA | GGC | AGC | ACC | CT | Tubulin | 3' splice junction intron 2 |
| 1281 SEQ ID NO:19 | ATG | ATA | ACT | GCA | TGA | TGT | TG | Aspartate protease | initiation of translation |
| 1282 SEQ ID NO:20 | GGA | AGG | ATT | CCC | GTG | TGC | GG | Aspartate protease | position 585 |
| 1283 SEQ ID NO:21 | AAC | AAT | ACC | TAA | ACC | TTG | GA | Aspartate protease | transcriptional terminator |

TABLE 1-continued

Antisense Oligonucleotides Targeted to *Candida Albicans*

| COMPOUND | | SEQUENCE (5'-3') | | | | | | TARGET RNA | |
|---|---|---|---|---|---|---|---|---|---|
| 1284 | SEQ ID NO:22 | ACC | ACC | GTC | CAT | TTT | GAA TG | Actin | initiation of transcription |
| 1285 | SEQ ID NO:23 | TTA | AAA | CAT | ACA | CCG | TCC A | Actin | 5' splice site |
| 1286 | SEQ ID NO:24 | CTA | TAA | AAA | TGG | GTT | GTA AT | Actin | branch and 3' splice site |
| 1287 | SEQ ID NO:1 | TGT | TGT | CGA | TAA | TAT | TAC CA | Chitin synthetase | initiation of translation |
| 1288 | SEQ ID NO:25 | GTG | TAT | GTC | ATG | TTG | GTA AA | Chitin synthetase | 2nd in-frame met |
| 1289 | SEQ ID NO:26 | TTT | AGC | TCT | AAC | ATC | ACC AC | Chitin synthetase | termination of translation |

*Candida albicans* is grown in a standard broth, such as Sabouraud dextrose broth (Difco) or yeast nitrogen base with glucose added. Candida is grown in 1 ml of solution and the antisense oligonucleotide compound is added at 50 µM and one half log dilutions thereof. Triplicate tubes are prepared for each dose. Inhibition of Candida growth is expected to occur with an I.C.$_{50}$ of 1–10 µM oligonucleotide compound.

Example 2

Synthesis and Characterization of Oligonucleotides:

Unmodified DNA oligonucleotides were synthesized on an automated DNA synthesizer (Applied Biosystems model 380B) using standard phosphoramidite chemistry with oxidation by iodine. β-cyanoethyldiisopropyl-phosphoramidites were purchased from Applied Biosystems (Foster City, Calif.). For phosphorothioate oligonucleotides, the standard oxidation bottle was replaced by a 0.2M solution of 3H-1,2-benzodithiole-3-one 1,1-dioxide in acetonitrile for the stepwise thiation of the phosphite linkages. The thiation cycle wait step was increased to 68 seconds and was followed by the capping step.

After cleavage from the controlled pore glass column (Applied Biosystems) and deblocking in concentrated ammonium hydroxide at 55° C. for 18 hours, the oligonucleotides were purified by precipitation twice out of 0.5M NaCl with 2.5 volumes ethanol. Analytical gel electrophoresis was accomplished in 20% acrylamide, 8M urea, 45 mM Tris-borate buffer, pH 7.0.

Oligodeoxynucleotides and their phosphorothioate analogs were judged from electrophoresis to be greater than 80% full length material.

Example 3

Germ Tube Assay For Antisense Oligonucleotide Inhibition of Candida:

The development of germ tubes, the initial stage in formation of hyphae, is believed to be important in allowing Candida to escape the effect of macrophages. Drugs that inhibit intracellular germ tube formation are potentially able to aid in host defense against Candida infection. Van't Wout et al., *J. Antimicrob. Chemotherapy*, 25:803 (1990).

*Candida albicans* is grown overnight in yeast nitrogen base (Difco Laboratories, Detroit, Mich.) supplemented with 0.15% asparagine and 2% dextrose. Cells are pelleted and washed twice with 1× PBS.

For analysis of acute effects, the final pellet is resuspended in DMEM plus 2% glucose at $5 \times 10^5$ cells/ml. 200 µl of this Candida suspension is added to wells in 96-well microtiter plates and oligonucleotides are added to desired concentrations. Plates are placed at 37° C. under 5% $CO_2$ and incubated for one hour. At the end of incubation, glutaraldehyde is added to 0.5% and plates are chilled to 4° C. Cells are examined microscopically and the percent of total cells with germ tubes formed is determined after counting three separate fields.

For analysis of effects of long-term exposure, cells are resuspended in YNB with 0.15% asparagine and 2% dextrose, and oligonucleotides are added. Plates are incubated for four hours at room temperature, after which cells are pelleted and washed in PBS. The final pellet is resuspended in DMEM plus 2% glucose and supplemented with fresh oligonucleotide. Cells are then incubated at 37° C. under 5% $CO_2$ and the germ tube assay performed as for analysis of short-term effects above.

The oligonucleotide analogs tested in germ tube assay for inhibition of *Candida albicans* are shown in Table 2:

TABLE 2

| SEQ ID NO: | ISIS # | 5' ... SEQUENCE ... 3' | TARGET | TYPE |
|---|---|---|---|---|
| 1 | 2214 | TGT TGT CGA TAA TAT TAC CA | Chitin synthetase AUG | P = O |
| 1 | 2216 | TGT TGT CGA TAA TAT TAC CA | " | P = S |
| 2 | 2215 | CAA TTT CTC TCA TAG TTC TA | β-Tubulin AUG | P = O |
| 2 | 2217 | CAA TTT CTC TCA TAG TTC TA | " | P = S |
| 3 | 2754 | TCA CTG GAT GGA GCC ATT TTC | Ribosomal L25 AUG | P = O |
| 4 | 2839 | CAC TGG ATG CAC CCA TTT TGT | Ribosomal L25 AUG | P = O |
| 4 | 2845 | CAC TGG ATG CAC CCA TTT TGT | " | P = S |
| 5 | 2933 | CTC ATA GTT CTA TAA TGT TGA | β-Tubulin AUG | P = S |
| 6 | 2938 | TGT TGT GCA TAA TAT TAC CA | Chitin synthetase AUG | P = S |
| 7 | 3156 | TTT ACC CAT GAT TGA TTA TAT | TEF1 and TEF2 AUG | P = O |

TABLE 2-continued

| SEQ ID NO: | ISIS # | 5'...SEQUENCE...3' | TARGET | TYPE |
|---|---|---|---|---|
| 7 | 3122 | TTT ACC CAT GAT TGA TTA TAT | " | P = S |
| 8 | 3121 | TCA CTG GAT GGA GCC ATT TTG | Ribosomal L25 AUG | P = O |
| 9 | 3152 | TGA CAT GAT CAA TGG ATG ACA | ATPase subunit b AUG | P = O |
| 9 | 3125 | TGA CAT GAT CAA TGG ATG ACA | " | P = S |
| 10 | 3150 | GTG CAT AAT ATT ACC ATC AAT | Chitin synthetase AUG | P = S |
| 11 | 3151 | AGC CAT ATT GAG TTA TGA TCT | Cytochrome P450 L1A1 AUG | P = S |
| 12 | 1049 | GCC GAG GTC CAT GTC GTA CGC | Control- HSV UL13 | P = O |
| 12 | 1082 | GCC GAG GTC CAT GTC GTA CGC | " | P = S |

Figure 2A:
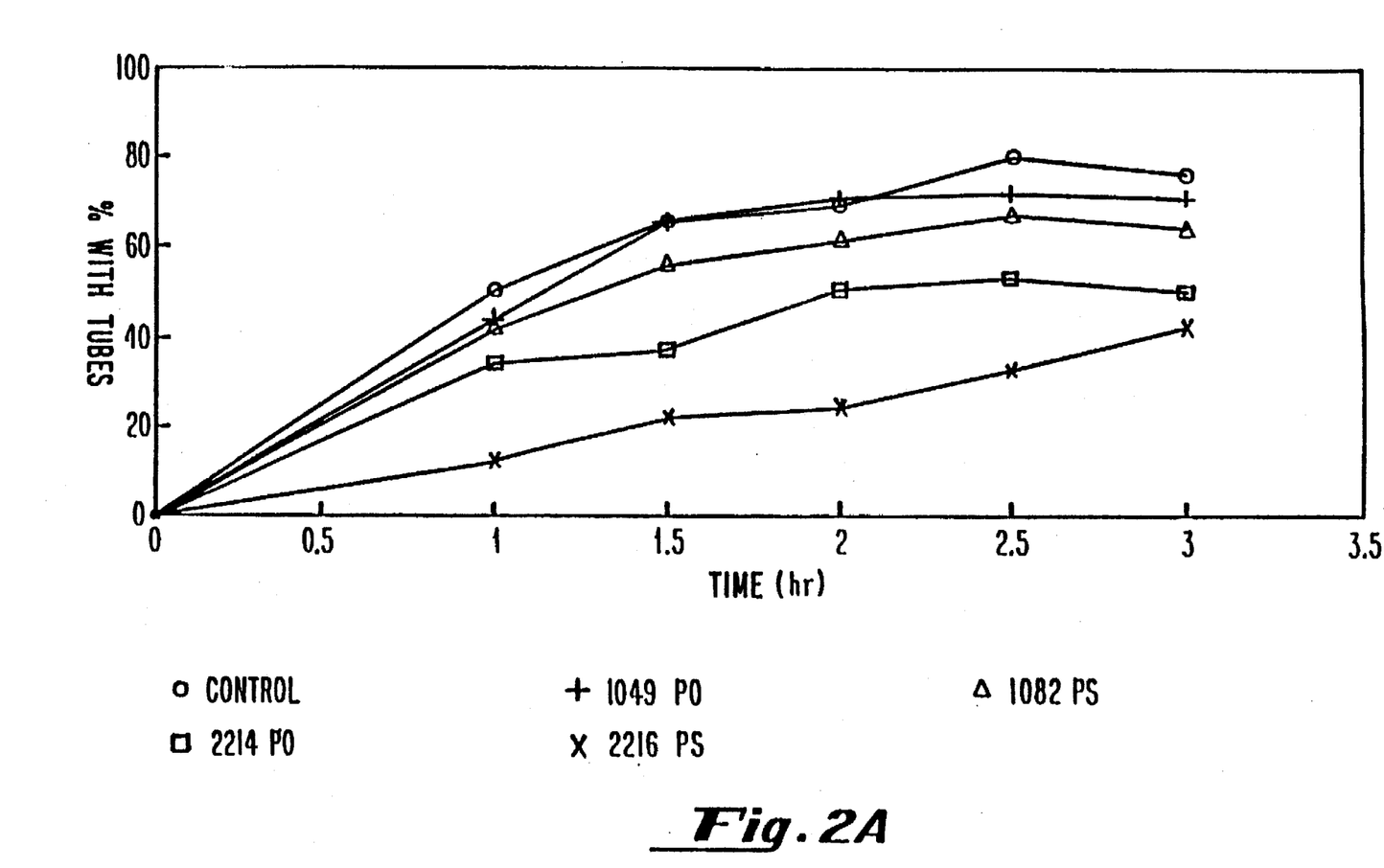
Figure 2B:
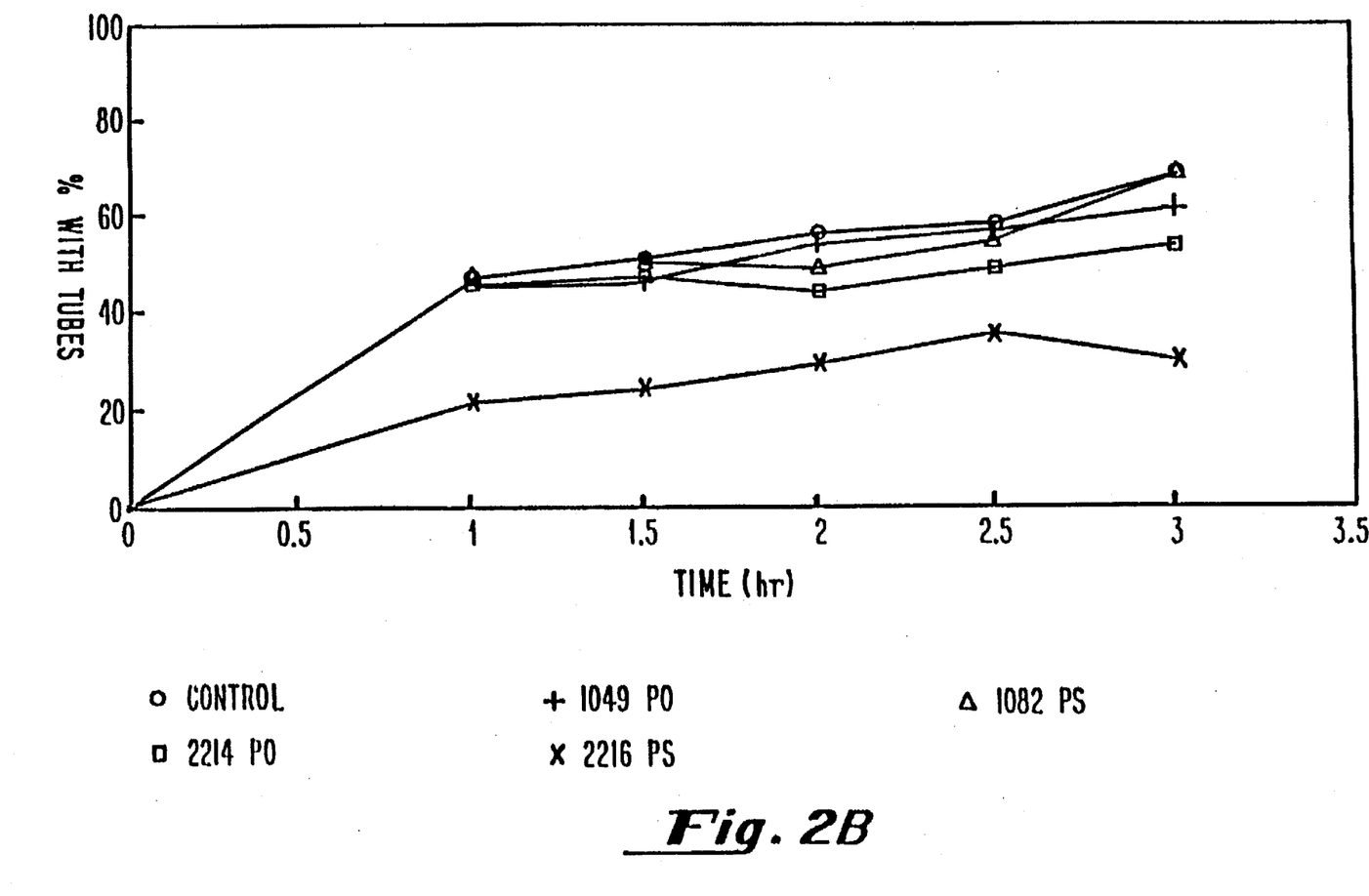

FIGS. 2A and B show the results of a time course analysis comparing the effects of antisense oligonucleotides (phosphodiester and phosphorothioate analog) specifically hybridizable with the chitin synthetase gene of *Candida albicans* with several controls. ISIS 2214 (SEQ ID NO: 1) is the phosphodiester oligonucleotide targeted to the AUG region of chitin synthetase. ISIS 2216 (SEQ ID NO: 1) is the phosphorothioate analog of ISIS 2214. ISIS 1049 and ISIS 1082 (SEQ ID NO: 12) are the phosphorodiester and phosphorothioate analog, respectively, of a control sequence hybridizable with a translation initiation codon of the mRNA product of the herpes simplex virus UL13 gene. "Control" indicates untreated cells. Results of germ tube assays at two doses of oligonucleotides, 0.5 and 1.0 μM, are shown in FIG. 2(A) and FIG. 2(B), respectively. At both doses, ISIS 2216, the phosphorothioate oligonucleotide analog hybridizable with mRNA encoding Candida chitin synthetase, showed a greater inhibition of Candida germ tube formation relative to the other compounds.

What is claimed is:

1. A synthetic oligonucleotide comprising a nucleotide sequence selected from the group consisting of SEQ ID NO:1, SEQ ID NO:2 and SEQ ID NO:7.

2. The oligonucleotide of claim 1, wherein said nucleotide sequence is SEQ ID NO:1.

3. The oligonucleotide of claim 1, wherein said nucleotide sequence is SEQ ID NO:2.

4. The oligonucleotide of claim 1, wherein said nucleotide sequence is SEQ ID NO:7.

5. The oligonucleotide of claim 1 in a pharmaceutically acceptable carrier.

6. The oligonucleotide of claim 1 wherein at least some of the linking groups between nucleotides of the oligonucleotide comprise sulfur-containing species.

7. The oligonucleotide of claim 1 wherein at least some of the linking groups between nucleotides of the oligonucleotide comprise phosphorothioate moieties.

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:1:

TGTTGTCGAT AATATTACCA  20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:2:

CAATTTCTCT CATAGTTCTA  20

( 2 ) INFORMATION FOR SEQ ID NO:3:

( i ) SEQUENCE CHARACTERISTICS:
        ( A ) LENGTH: 21 base pairs (B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:3:

TCACTGGATG GAGCCATTTT C             21

(2) INFORMATION FOR SEQ ID NO:4:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:4:

CACTGGATGC ACCCATTTTG T             21

(2) INFORMATION FOR SEQ ID NO:5:

(i) SEQUENCE CHARACTERISTICS:
(A) LENGTH: 21 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:5:

CTCATAGTTC TATAATGTTG A             21

(2) INFORMATION FOR SEQ ID NO:6:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:6:

TGTTGTGCAT AATATTACCA               20

(2) INFORMATION FOR SEQ ID NO:7:

(i) SEQUENCE CHARACTERISTICS:
(A) LENGTH: 21 base pairs
(B) TYPE: nucleic acid
(C) STRANDEDNESS: single
(D) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:7:

TTTACCCATG ATTGATTATA T                                                                                            2 1

( 2 ) INFORMATION FOR SEQ ID NO:8:

( i ) SEQUENCE CHARACTERISTICS:
                      ( A ) LENGTH: 21 base pairs
                      ( B ) TYPE: nucleic acid
                      ( C ) STRANDEDNESS: single
                      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:8:

TCACTGGATG GAGCCATTTT G                                                                                            2 1

( 2 ) INFORMATION FOR SEQ ID NO:9:

( i ) SEQUENCE CHARACTERISTICS:
                      ( A ) LENGTH: 21 base pairs
                      ( B ) TYPE: nucleic acid
                      ( C ) STRANDEDNESS: single
                      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:9:

TGACATGATC AATGGATGAC A                                                                                            2 1

( 2 ) INFORMATION FOR SEQ ID NO:10:

( i ) SEQUENCE CHARACTERISTICS:
                      ( A ) LENGTH: 21 base pairs
                      ( B ) TYPE: nucleic acid
                      ( C ) STRANDEDNESS: single
                      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:10:

GTGCATAATA TTACCATCAA T                                                                                            2 1

( 2 ) INFORMATION FOR SEQ ID NO:11:

( i ) SEQUENCE CHARACTERISTICS:
                      ( A ) LENGTH: 21 base pairs
                      ( B ) TYPE: nucleic acid
                      ( C ) STRANDEDNESS: single
                      ( D ) TOPOLOGY: linear ( i i ) MOLECULE TYPE: cDNA ( i i i ) HYPOTHETICAL: NO (i v) ANTI-SENSE: YES (x i) SEQUENCE DESCRIPTION: SEQ ID NO:11:

AGCCATATTG AGTTATGATC T 21

(2) INFORMATION FOR SEQ ID NO:12:

(i) SEQUENCE CHARACTERISTICS:
        (A) LENGTH: 21 base pairs
        (B) TYPE: nucleic acid
        (C) STRANDEDNESS: single
        (D) TOPOLOGY: linear     (i i) MOLECULE TYPE: cDNA     (i i i) HYPOTHETICAL: NO     (i v) ANTI-SENSE: YES     (x i) SEQUENCE DESCRIPTION: SEQ ID NO:12:

GCCGAGGTCC ATGTCGTACG C 21

(2) INFORMATION FOR SEQ ID NO:13:

(i) SEQUENCE CHARACTERISTICS:
        (A) LENGTH: 1888 base pairs
        (B) TYPE: nucleic acid
        (C) STRANDEDNESS: single
        (D) TOPOLOGY: linear     (i i) MOLECULE TYPE: cDNA     (i i i) HYPOTHETICAL: NO     (i v) ANTI-SENSE: YES     (x i) SEQUENCE DESCRIPTION: SEQ ID NO:13:

```
TTATATCAAA TAGATTTAGA TTTTTTATT  TTAAAGAATT TTTTAATCAA GAAATCAATA      60
TCAACATTAT AGAACTATGA GAGAAATTGT ATGTTCCGTT TATTCCCTTC CTTACACCAA     120
ATCATTGGAA TCCTTATGTG TTTTGTTGTT GTTGTCTGAA AATTTTGGT  TCTGTTTTAC     180
GCGCCTTTTT CGACTAAATT GATTCAAATA GGATTCCCTA ATGATTAAT  GATTTGTGTC     240
AATCAATCAA TGTTTTATTA AGTTTATCA  AATATACTAA CTGCTTTTGC CCTTTTTTTT     300
AGATTCATTT ATCAACTGGT CAATGTGGTA ATCAAATTGT ATGTATAAAC ACTGAAGAAA     360
AAAAAATTCT ATCATTGTTA TGTTGTGATC TTTGATCTTT AGTTGTCGGG TTAACACCTG     420
CCAATTGGAT CAATACATCA ATCAATTAAT TCTAATCTTG AAAAAAAAAT TGATTTTACT     480
AACAATTTTT TCTTTTATTT AGGGTGCTGC CTTTTGGGAA ACTATTTGTG GAGAACATGG     540
ATTAGATAAC AATGGAACTT ATGTTGGAAA TAATGAACTT CAAAAATCCA AATTAGACGT     600
TTATTTCAAC GAAGCTACTT CTGGGAAATA CGTTCCTCGT GCCGTTTTAG TCGATTTGGA     660
ACCAGGTACT ATTGATAATG TGAAAACTTC ACAAATTGGT AACTTGTTTA GACCAGATAA     720
CTTTATTTTC GGTCAAAGTT CTGCCGGCAA TGTTTGGGCT AAAGGTCATT ACACTGAAGG     780
TGCTGAATTA GTTGATTCTG TTTTAGATGT TGTTAGAAGA GAAGCTGAAG GCTGTGATTC     840
TTTACAAGGT TTCCAAATCA CCCATTCTTT GGGTGGTGGT ACTGGTTCTG GTATGGGTAC     900
TTTGTTGATT TCTAAAATTA GAGAAGAATT CCCTGATACA ATGATGGCCA CTTTTTCTGT     960
TGTCCCATCA CCAAAAGTTT CCGATACCGT TATTGAACCA TATAACGCTA CTTTATCAGT    1020
CCATCAATTG GTTGAAAACT CTGATGAAAC TTTCTGTATT GATAATGAAG CCTTGTACAA    1080
TATTTGTCAA AACACTTTGA AATTACCACA ACCATCTTAT GCTGAATTGA ACAATTTGGT    1140
```

| | | | | | | |
|---|---|---|---|---|---|---|
| TTCTTCTGTC | ATGTCTGGTG | TTACTACTTC | TTTACGTTAT | CCAGGTCAAT | TGAATTCGGA | 1200 |
| TTTAAGAAAA | TTGGCAGTCA | ATTTGGTTCC | ATTCCCAAGA | TTACATTTCT | TTATGGTTGG | 1260 |
| TTATGCTCCA | TTGACTTCTA | TGGGTTCTAA | ATCTTTCAGA | TCAGTCACCG | TCCCAGAATT | 1320 |
| GACTCAACAA | ATGTTTGATG | CCAAAAATAT | GATGGCTGCT | TCTGATCCAA | GAAATGGTCG | 1380 |
| TTATTTAACT | GTTGCTGCCT | TTTTCAGAGG | TAAAGTATCT | GTTAAAGAAG | TTGACGATGA | 1440 |
| AATGCACAAA | ATCCAAACCA | GAAACTCATC | TTATTTTGTT | GATTGGATTC | CAAATAATGT | 1500 |
| TCAAACTGCT | GTTTGTTCAG | TTCCTCCAAA | AGATTTGGAT | ATGTCTGCTA | CTTTTATTGG | 1560 |
| AAACTCTACT | TCCATTCAAG | AATTATTTAA | AAGAGTTGGT | GATCAATTCA | GTGCTATGTT | 1620 |
| CAGAAGAAAA | GCTTTCTTGC | ATTGGTATAC | TTCTGAAGGT | ATGGATGAAA | TGGAATTTAC | 1680 |
| TGAAGCTGAA | TCTAATATGA | ATGATTTGGT | TAGTGAATAC | CAACAATACC | AAGAAGCTAG | 1740 |
| TATTGATGAA | GAAGAATTAG | AATATGCCGA | TGAAATCCCA | TTAGAAGATG | CCGCCATGGA | 1800 |
| ATAAAAGCTG | ATAAATGCTA | CAATATTAAT | TAATTATAAT | TTTTTTTTTT | GTTCACTTCT | 1860 |
| AATATAATTA | TGGTTTTTTT | TGGTTTAG | | | | 1888 |

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:14:

CGGAACATAC AATTTCTCTC        20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:15:

CAAAAGCAGT TAGTATATTT        20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear     ( i i ) MOLECULE TYPE: cDNA     ( i i i ) HYPOTHETICAL: NO     ( i v ) ANTI-SENSE: YES     ( x i ) SEQUENCE DESCRIPTION: SEQ ID NO:16:

AAAAATTGTT AGTAAAATCA                                                           20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:17:

CTAAAAAAAA GGGCAAAAGC                                                           20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:18:

TTCCCAAAAG GCAGCACCCT                                                           20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:19:

ATGATAACTG CATGATGTTG                                                           20

( 2 ) INFORMATION FOR SEQ ID NO:20:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:20:

GGAAGGATTC CCGTGTGCGG                                                           20

( 2 ) INFORMATION FOR SEQ ID NO:21:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:21:

AACAATACCT AAACCTTGGA                                          20

( 2 ) INFORMATION FOR SEQ ID NO:22:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:22:

ACCACCGTCC ATTTTGAATG                                          20

( 2 ) INFORMATION FOR SEQ ID NO:23:

( i ) SEQUENCE CHARACTERISTICS:
      ( A ) LENGTH: 19 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:23:

TTAAAACATA CACCGTCCA                                           19

( 2 ) INFORMATION FOR SEQ ID NO:24:

( i ) SEQUENCE CHARACTERISTICS:
      ( A ) LENGTH: 20 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: YES ( x i ) SEQUENCE DESCRIPTION: SEQ ID NO:24:

CTATAAAAAT GGGTTGTAAT                                          20

( 2 ) INFORMATION FOR SEQ ID NO:25:

( i ) SEQUENCE CHARACTERISTICS:
      ( A ) LENGTH: 20 base pairs (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:25:

GTGTATGTCA TGTTGGTAAA                                                                 20

(2) INFORMATION FOR SEQ ID NO:26:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (xi) SEQUENCE DESCRIPTION: SEQ ID NO:26:

TTTAGCTCTA ACATCACCAC                                                                 20